United States Patent
Capewell

(10) Patent No.: US 8,150,115 B2
(45) Date of Patent: Apr. 3, 2012

(54) CHEMISTRY STRIP READER AND METHOD

(75) Inventor: Dale Capewell, Agoura Hills, CA (US)

(73) Assignee: Iris International, Inc., Chatsworth, CA (US)

( * ) Notice: Subject to any disclaimer, the term of this patent is extended or adjusted under 35 U.S.C. 154(b) by 860 days.

(21) Appl. No.: 12/105,184

(22) Filed: Apr. 17, 2008

(65) Prior Publication Data

US 2008/0267445 A1    Oct. 30, 2008

Related U.S. Application Data

(60) Provisional application No. 60/925,232, filed on Apr. 18, 2007.

(51) Int. Cl.
  *G06K 9/00* (2006.01)
  *G01N 21/00* (2006.01)
(52) U.S. Cl. ........ 382/128; 422/82.05; 436/44; 436/164
(58) Field of Classification Search .................. 382/100, 382/128; 702/22, 32; 436/44, 164; 422/82.05, 422/82.09; 435/970
See application file for complete search history.

(56) References Cited

U.S. PATENT DOCUMENTS

| | | | |
|---|---|---|---|
| 3,910,701 A | 10/1975 | Henderson et al. | 356/39 |
| 4,676,653 A | 6/1987 | Strohmeier et al. | 356/446 |
| 4,717,546 A | 1/1988 | Barnett | 422/63 |
| 5,143,694 A | 9/1992 | Schafer et al. | 422/65 |
| 5,378,630 A | 1/1995 | Kai et al. | 436/43 |
| 5,408,535 A | 4/1995 | Howard, III et al. | 382/1 |
| 5,477,326 A | 12/1995 | Dosmann | 356/406 |
| 5,504,317 A | 4/1996 | Takahashi | 235/462 |
| 5,508,200 A | 4/1996 | Tiffany et al. | 436/44 |
| 5,563,042 A | 10/1996 | Phillips et al. | 435/14 |
| 5,597,532 A | 1/1997 | Connolly | 422/58 |
| 5,686,047 A | 11/1997 | Augstein | 422/65 |
| 5,846,490 A | 12/1998 | Yokota et al. | 422/66 |
| 5,995,236 A | 11/1999 | Roth et al. | 356/445 |
| 6,027,692 A | 2/2000 | Galen et al. | 422/82.05 |
| 6,201,607 B1 | 3/2001 | Roth et al. | 356/445 |
| 6,235,241 B1 | 5/2001 | Catt et al. | 422/56 |
| 6,261,522 B1 | 7/2001 | Hough et al. | 422/82.05 |
| 6,267,722 B1 | 7/2001 | Anderson et al. | 600/300 |
| 6,541,266 B2 | 4/2003 | Modzelewski et al. | 436/95 |
| 6,847,451 B2 | 1/2005 | Pugh | 356/436 |
| 6,895,263 B2 | 5/2005 | Shin et al. | 600/316 |
| 6,947,586 B2 | 9/2005 | Kasdan et al. | 382/133 |
| 7,197,169 B2 | 3/2007 | Wang | 382/128 |
| 7,344,081 B2 | 3/2008 | Tseng | 235/462.13 |
| 7,390,665 B2 | 6/2008 | Gilmour et al. | 436/44 |
| 7,537,733 B2 | 5/2009 | Lappe et al. | 422/82.05 |
| 2007/0086004 A1 | 4/2007 | Maier et al. | 356/301 |
| 2008/0267446 A1 | 10/2008 | Capewell | 382/100 |
| 2011/0096160 A1 | 4/2011 | Capewell | 348/135 |

FOREIGN PATENT DOCUMENTS

| | | |
|---|---|---|
| JP | 07-005110 A | 10/1995 |
| JP | 2001-183309 A | 6/2001 |

OTHER PUBLICATIONS

International Search Report and Written Opinion of the International Search Authority; dated Jul. 25, 2008, received in the corresponding PCT application PCT/US2008/005006, 7 pages.
Notification Concerning Transmittal Of Copy Of International Preliminary Report On Patentability, dated Oct. 29, 2009, received in the corresponding PCT application PCT/US2008/005006, 10 pages.
International Search Report And Written Opinion of the International Search Authority; dated Jul. 25, 2008, received in the corresponding PCT application PCT/US2008/005043, 9 pages.
Notification Concerning Transmittal Of Copy Of International Preliminary Report On Patentability, dated Oct. 29, 2009, received in the corresponding PCT application PCT/US2008/005043, 6 pages.

*Primary Examiner* — Andrew W Johns
(74) *Attorney, Agent, or Firm* — DLA Piper LLP (US)

(57) ABSTRACT

A chemistry strip reader and method for analyzing chemistry strips. A conveyor moves chemical strips through different imaging positions at discrete points in time across the field of view of a camera, which captures images of each chemistry strip at different discrete times. A processor determines reflectance values for each of the chemical strips from the captured images at the discrete points in time. Calibration targets adjacent the chemistry strips can be used to adjust the determined reflectance values. The light source can sequentially illuminate each chemistry strip with three different wavelengths of light, where the processor calculates a concentration determination associated with the chemistry strip by calculating different chromaticity coordinates for the different wavelengths of light, and comparing them to known chromaticity coordinates for known analyte concentrations.

13 Claims, 5 Drawing Sheets

CHEMISTRY STRIP READER AND METHOD

RELATED APPLICATIONS

This application claims the benefit of U.S. Provisional Application No. 60/925,232, filed Apr. 18, 2007, and which is incorporated herein by reference.

FIELD OF THE INVENTION

The present invention relates to sample solution analysis, and in particular to a chemistry strip reader and a method of reading chemistry strips for analyzing sample solutions.

BACKGROUND OF THE INVENTION

Currently, chemistry strips (also known as chemical strips) are in common use to test for the presence of certain chemicals in a sample solution. Typically, a single chemistry strip includes a plurality of test (chemistry) pads which are exposed to the sample to be tested. A set amount of time is allowed to pass, and then a change in the color or level of reflectance of the chemistry strip pads is measured. For example, chemistry strips for urinalysis are designed to operate on the basic premise that each test pad changes color depending on the concentration of the relevant analyte that reacts with that pad. A color chart is used to visually read the chemistry strips. The chart indicates the color of each test pad depending on the analyte concentration of the dosed sample. The original "strip reader" for chemistry strips was the human eye. The chemistry strip was held next to the color chart to assess which square on the color chart most closely matched the color on the pad, and the corresponding analyte concentration for the square on the color chart was manually recorded. This technique remains common today despite the human subjectivity of the process.

Optoelectronic strip readers have been developed to help automate the chemistry strip reading process and eliminate the subjectivity of the human observer. Most optoelectronic strip readers are basically reflectometers, that is, instruments that measure optical reflectance from the chemistry strip pads. This is done by illuminating the pad with a light source such as an LED, measuring the reflected light using a photodiode or other sensor, and comparing the result to known standards. An LED having a fairly narrow wavelength spectrum (e.g. typically about 40 nm) and a given peak wavelength is selected to maximize the change in reflectance signal vs. analyte concentration. Since the optimal wavelength is different for different chemistries, optoelectronic strip readers may employ several different color LEDs and use the various colors to measure reflectance from the chemistry pads. For typical optoelectronic strip readers, therefore, the differentiation between samples having different analyte concentrations is made by measuring differences in optical reflectance from the appropriate chemistry pad using the appropriate color LED to illuminate it.

The assumption made with conventional LED/photodiode based reflectometers to differentiate changes in color on a chemistry strip pad is that the observed change is primarily a change in brightness rather than a change in hue or saturation. For some chemistry strip pads this may be true, but for others it is not. Further, conventional reflectometers measure the reflectance of all test pads after a specific incubation period (i.e. an "end point" measurement. However, different pads may react at different rates. Further, higher concentrations of the tested material in the sample should be tested using a shorter incubation period, while lower concentrations of the tested material in the sample should be tested using a longer incubation period. By automating the inspection process so that a single measurement is taken only after incubation is complete for all pads, data that can be used to better determine material concentration levels is lost.

SUMMARY OF THE INVENTION

The aforementioned issues are addressed by providing a chemistry strip reader and method which captures chemistry strip reflectance and determines a concentration value based upon chemistry strip reflectances captured over time.

A chemistry strip reader for analyzing chemistry strips includes a conveyor having a surface for supporting a plurality of chemical strips in a plurality of imaging positions and for moving the chemical strips through the imaging positions at discrete points in time, a camera for capturing images of a field of view that includes the plurality of imaging positions and any of the chemistry strips therein, wherein the images are captured at the discrete points in time, and a processor for determining reflectance values for each of the chemical strips from the captured images at the discrete points in time.

A method of analyzing a chemistry strip includes capturing a plurality of images of a chemistry strip at discrete points in time, determining reflectance values for the chemical strip from the captured images, fitting the determined reflectance values for the chemical strip to a curve defined by $A \exp[-B(t+t_o)]+C$, where A, B, C, and to are fit parameters, and calculating a concentration determination associated with the chemical strip by determining a first slope of the curve for $t=-t_o$ and comparing the first slope with known first slopes for given analyte concentrations.

Additionally, a method of analyzing a chemistry strip includes placing a chemistry strip on a support surface of a conveyor, moving the conveyor surface to sequentially move the chemistry strip to a plurality of imaging positions at discrete times, capturing an image of the chemistry strip at each of the imaging positions, determining reflectance values for the chemical strip from the captured images, fitting the determined reflectance values for the chemical strip to a curve defined by $A \exp[-B(t+t_o)]+C$, where A, B, C, and to are fit parameters, and calculating a concentration determination associated with the chemical strip by determining a first slope of the curve for $t=-t_o$ and comparing the first slope with known first slopes for given analyte concentrations.

Other objects and features of the present invention will become apparent by a review of the specification, claims and appended figures.

DETAILED DESCRIPTION OF THE PREFERRED EMBODIMENTS

Figure 1:
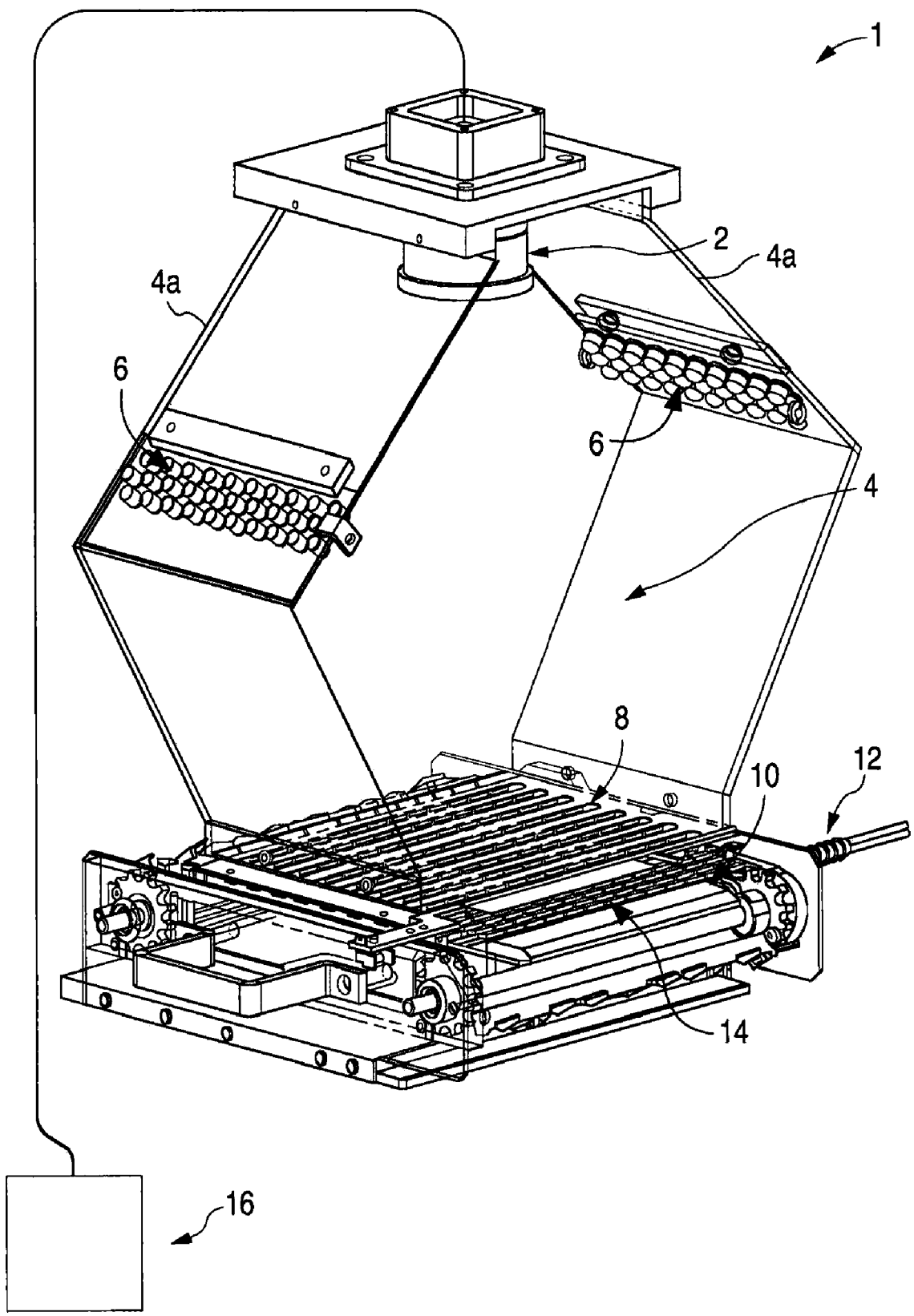
FIG. 1 is a perspective view of the chemistry strip reader of the present invention.

The chemistry strip reader 1 of the present invention is shown in FIG. 1, and includes a camera 2, a housing 4, light source 6, calibration target 8, conveyor 10 and heating device 12 for conveying and heating chemistry strips 14, and a processor 16.

Housing 4 encloses an area above conveyor 10. Light source 6 is inside the area contained by housing 4, where the bottom of housing 4 is open to allow light from light source or sources 6 to reflect off of chemical strip 14 that sits on the conveyor 10. Camera 2 is positioned to capture images of chemical strips 14 as they move along conveyor 10. The invention may contain one or more calibration targets 8, which allow results to be normalized for different cameras, variations in camera response over time, heat changes, or other variables. The chemistry strip reader 1 may also contain a heating device 12 for maintaining the chemistry strips 14 at a constant temperature as their images are recorded over time and/or ensure that multiple chemistry strips 14 are all analyzed at the same temperature.

Camera 2 may be a CMOS sensor, a CCD sensor, or any other camera device capable of recording an image of the appropriate wavelength. In one embodiment, the camera 2 contains internal memory for storing images. In another embodiment, the camera is connected to a processor 16 for storage or processing of the camera images.

Light source 6 may be any light source capable of creating the appropriate wavelength or wavelengths necessary for even illumination of the chemistry strips 14 and calibration targets 8 such that camera 6 can capture the images of, and measure the reflectance of, chemistry strips 14. For example, light source 6 can comprise rows of LEDs of alternating color, such as alternating red, green, and blue LEDs. Alternating the relative positioning of the colored LEDs provides better uniformity of illumination for each of the colors, compared to positioning like-colored LEDs together. Additionally, the LEDs of light source 6 are each preferably covered with a light diffuser cap, to more evenly illuminate the chemistry strips 14 below. Alternately, each diffuser cap can cover groups of LEDs of different colors. The field of view 22 of camera 2 is illuminated from above by light source(s) 6 which are preferably pulsed and synchronized to the shutter of the camera 2.

Figure 5:
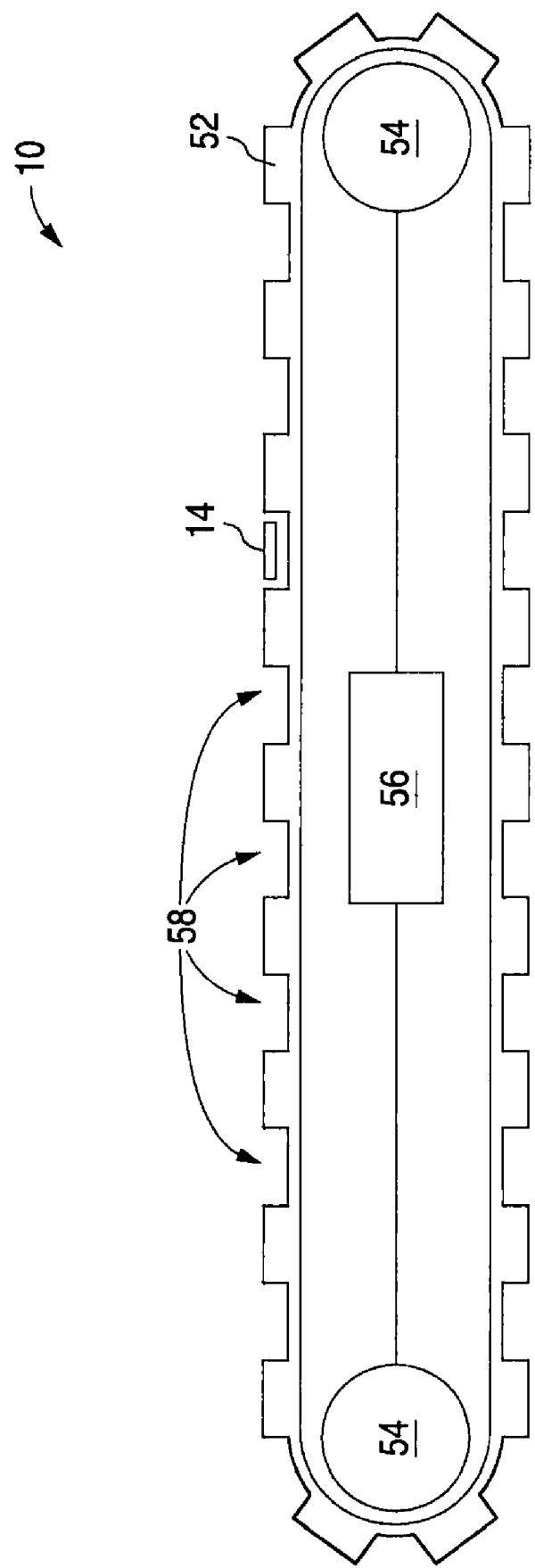
FIG. 5 is a side cross-sectional view of the conveyor belt for moving the chemistry strips along imaging positions in the camera's field of view.

Conveyor 10, can be any appropriate mechanism for moving chemistry strips 14 across the camera's field of view. As shown in FIG. 5, conveyor 10 comprises a belt 52 wrapped around wheels 54. The wheels 54 are powered by a motor 56 which spins the wheels 54, causing the surface of the belt 52 to move, and chemistry strips 14 to move along with the surface of the belt 52. The belt contains slots 58 each for holding a chemistry strip 14 in a fixed position on the belt 52 as the belt moves.

Housing 4 is a structure above the surface of the conveyor 10. The housing 4 may contain mounting attachments for holding camera 2 over conveyor 10. Housing 4 has top panels 4a arranged off angle from the surface of conveyor 10 such that light source 6 mounted thereto is positioned to avoid specular reflection from the conveyor 10, chemistry strips 14 and calibration targets 8 (as well as other surfaces forming housing 4). The internal surfaces of housing 4 are preferably white, in order to further diffuse the light, and to prevent images captured by camera 2 from having black edges.

Figure 2:
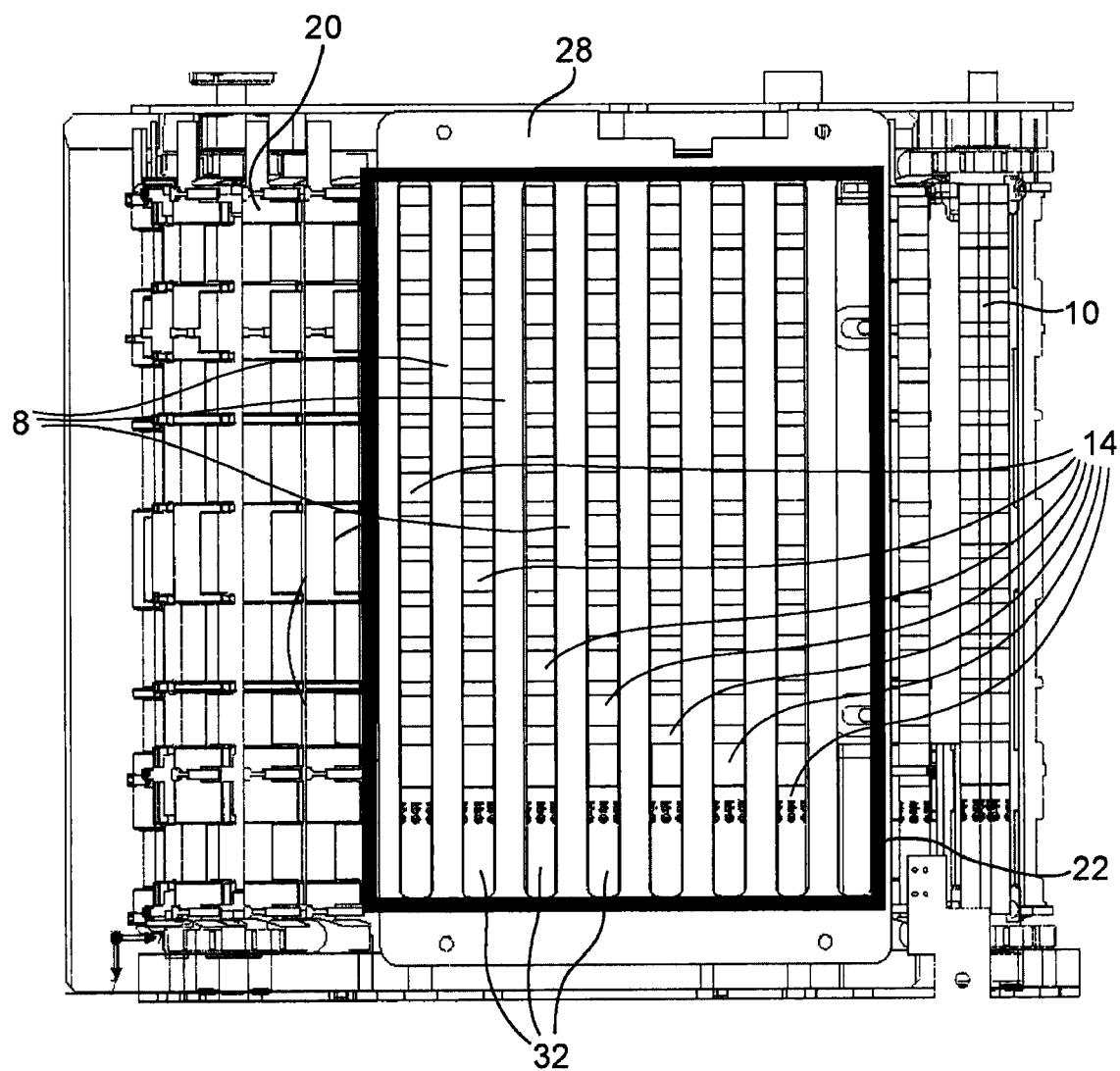
FIG. 2 is a top view of the chemistry reader showing the plane where the chemical strips move through the reader.

Calibration targets 8 are made of materials (or coatings) of known optical properties (i.e. known reflectance properties, such as standard Munsell values N5-N9) that provide known calibration images for camera 2 directly adjacent the chemistry strips 14 being analyzed. The image of the calibration targets 8 captured by camera 2 can be used to compensate and correct images captured by camera 2 of chemistry strips 14. The present invention contemplates taking multiple images of multiple chemistry strips 14 over time. Therefore, the calibration targets 8 can be configured as shown in FIG. 2, where a single plate 28 is positioned just above the surface of conveyor 10, with apertures 32 formed therein that define imaging locations where chemistry strips 14 can be illuminated by light source 6 and imaged by camera 2. The portions of plate 28 in-between the apertures 32 form the calibration targets 8 for the adjacent imaging locations. In the embodiment illustrated in FIG. 2, the plate 28 includes eight apertures 32 so that eight different chemistry strips 14 can be imaged at any instant in time. With chemistry strips 14 loaded at one end of the conveyor and removed at the other end of the conveyor, where the conveyor moves the chemistry strips from one aperture 32 to the next at even time intervals, each chemistry strip 14 can be imaged eight different times at eight different imaging locations as it moves across conveyor 10. As needed, the reflectance from any chemistry strip pad and a neighboring calibration target 8 can be compared to provide any necessary compensation to the image of the chemistry strip pad.

The processor 16 may be any processing device capable of receiving and processing the image data from the camera 2. The processor 16 may be a personal computer or a dedicated microprocessor, which receives data from camera 2 directly though a wire or cable, or via a portable memory device (e.g. USB flash memory card), or via a wireless connection, or via any other communication method. The processor 16 can include a neural network to aid in the processing of the image data from the chemistry strips and calibration targets 8.

In operation, chemistry strips 14 are sequentially exposed to a sample substance at known time intervals, with the purpose of testing for chemical concentrations at known time intervals during the incubation process. Specifically, a first chemistry strip 14 is dosed (exposed to the sample substance) and immediately placed in the first slot on conveyor 10. The conveyor 10 then moves the chemistry strip 14 to the first aperture 32 for imaging. A second chemistry strip 14 is dosed and immediately placed in the now vacant first slot, and both chemistry strips 14 are advanced to the next respective apertures 32 for imaging. A third chemistry strip 14 is dosed and placed in the now vacant first slot, and all three chemistry strips 14 are advanced to the next respective apertures 32 for imaging. This process continues until each of the chemistry strips 14 pass through all eight apertures 32 for imaging. The chemistry strip 14 in the last aperture 32 will have incubated for a time equal to the number of aperture positions on the plate 28 times the time delay between movements of the conveyor. For example, with eight positions and a delay of 15 seconds between conveyor movements, a maximum incubation time near 120 seconds is realized, along with a chemistry strip throughput of 240 per hour. The result is that each chemistry strip is imaged eight different times at eight discrete imaging locations, together with images of adjacent calibration targets 8, at eight known time intervals, all automatically.

Plate 28 and conveyor 10 are configured such that both the chemistry strips 14 and the calibration targets 8 are in the focal plane of a camera 2 suspended above the conveyor 10, and within the camera's field of view 22. Each time the chemistry strips 14 reach apertures 32, the interior of the housing 4 is illuminated with multiple wavelengths of light from light source(s) 6 at which time the camera 2 records images of the calibration targets 8 and the chemistry strips 14 seen through the apertures 32 in the plate 28. At each aperture 32 location, the chemistry strips 14 can be imaged once using single or multiple wavelength illumination from the fight source 6, or can be imaged multiple times each using a different wavelength or combination of wavelengths from the light source 6. For example, each time the conveyor 10 stops with chemistry strips 14 exposed by apertures 32, the chemistry strips 14 can be sequentially imaged using red light, then green light, then blue light, from the light source 6. Thus, in this example, each chemistry strip 14 traveling through all eight aperture locations is imaged three times at each location (using different illumination wavelengths), for a total of 24 images at a total of eight discrete time intervals within the incubation period. The heating device 12 maintains the chemistry strips 6 at a constant or uniform temperature as they move along conveyor 10 at the base of housing 4.

Images from camera 2 are sent to processor 16, which extracts or otherwise determines and processes reflectance data from the images. One processing analysis performed by processor 16 includes calculating "pseudo chromaticity" data from the reflectance data. For each wavelength the coordinate is equal to 100 times the reflectance value measured at that wavelength, divided by the sum of the reflectance values for all the wavelengths at which data was taken. For example, where images are collected for three wavelengths A, B and C at each aperture location, chromaticity coordinates are determined using the following three equations:

coordinate $A=100*A/(A+B+C)$ coordinate $B=100*B/(A+B+C)$ coordinate $C=100*C/(A+B+C)$.

The calculated pseudo-chromaticity coordinates are compared with a spine of data in this coordinate space, where each point on the spine of data correlates to a relevant analyte concentration.

Figure 3:
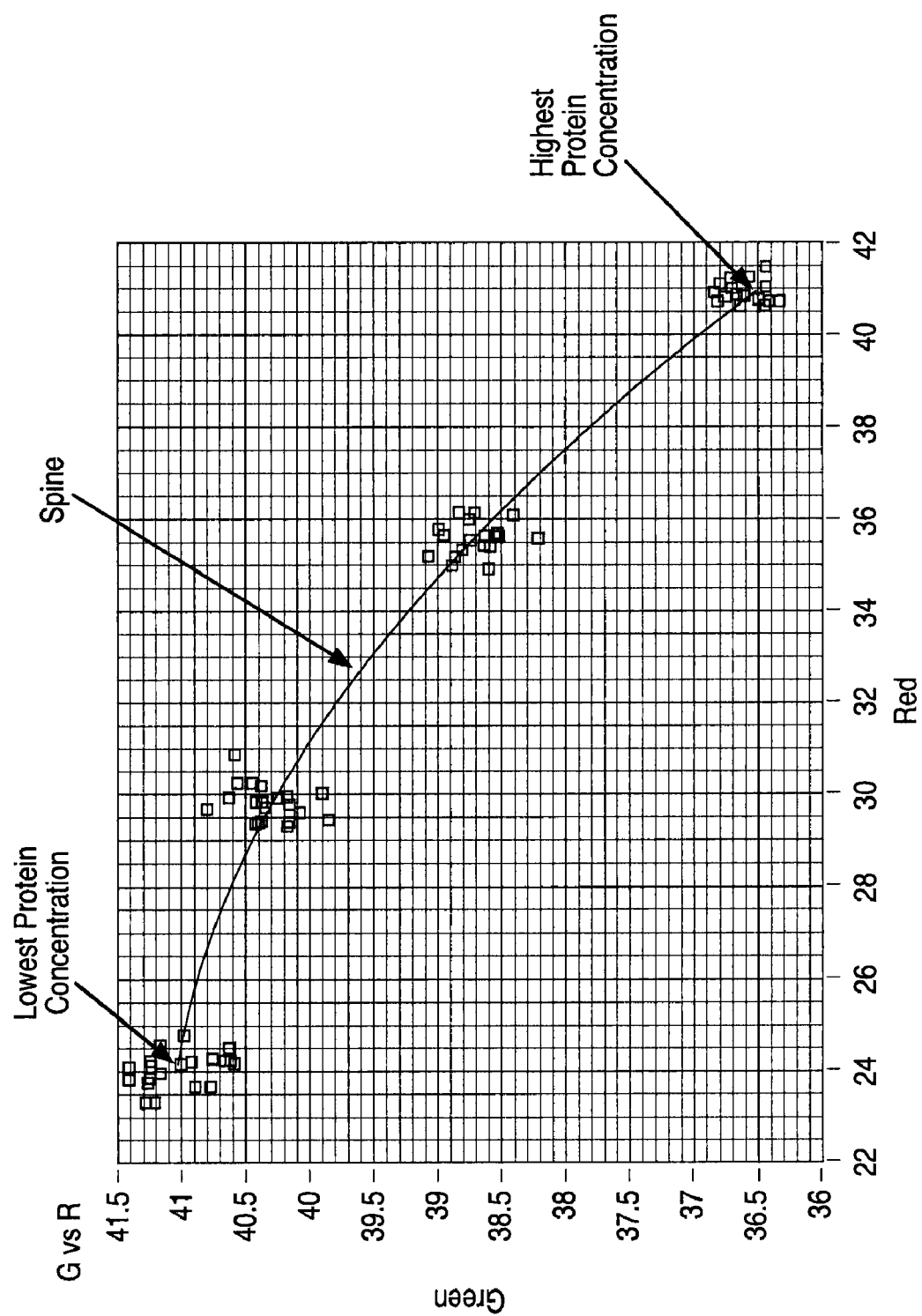
FIG. 3 is a graph showing a plot of pseudo chromaticity coordinates.

For example, FIG. 3 is a graph showing a plot of "pseudo chromaticity" coordinates (G vs R) obtained from 20 samples each having one of four different concentrations of protein. Thus, in this case, variables A, B, C in the above equations are red, green and blue, respectively. These coordinates were calculated by measuring the reflectance from a protein pad under red, green, and blue LED illumination (R, G, B, respectively) after 120 seconds of chemistry strip incubation, and then forming the coordinates Green=$100*G/(R+G+B)$ and Red=$100*R/(R+G+B)$. On a plot of Green vs Red, data acquired at like protein concentrations cluster together into separate groups along a spine that connects the centers of each concentration cluster. The R, G, B reflectance measurements from a pad dosed with a protein concentration between the lowest concentration and the highest concentration in FIG. 4 would be expected to result in a pair of "pseudo-chromaticity" coordinates lying along the length of the spine, proportionately spaced between these two extreme clusters. While only protein is depicted in FIG. 3, variation in concentration for each chemistry on the chemistry strip is expected to be characterized by a unique spine through this same "pseudo-chromaticity" space, or through (G vs. B) or (B vs. R) "pseudo-chromaticity" spaces.

A second processing analysis performed by processor 16 analyzes the reflectance data for a single chemistry strip 14 collected over time during the incubation period (i.e. from multiple images, where each image corresponds to reflectance data recorded at a different point in time). The processor 16 fits the data to a curve of the form:

$R(t)=A\exp[-B(t+t_o)]+C,$ where A, B, C, and to are all fit parameters. The processor 16 then compares the slope of the curve at time $t=-t_o$ with slopes for known analyte concentrations for the given analyte, and compares the asymptotic value of R(t) (which is equal to C) with that for known analyte concentrations, to make a concentration determination.

Figure 4:
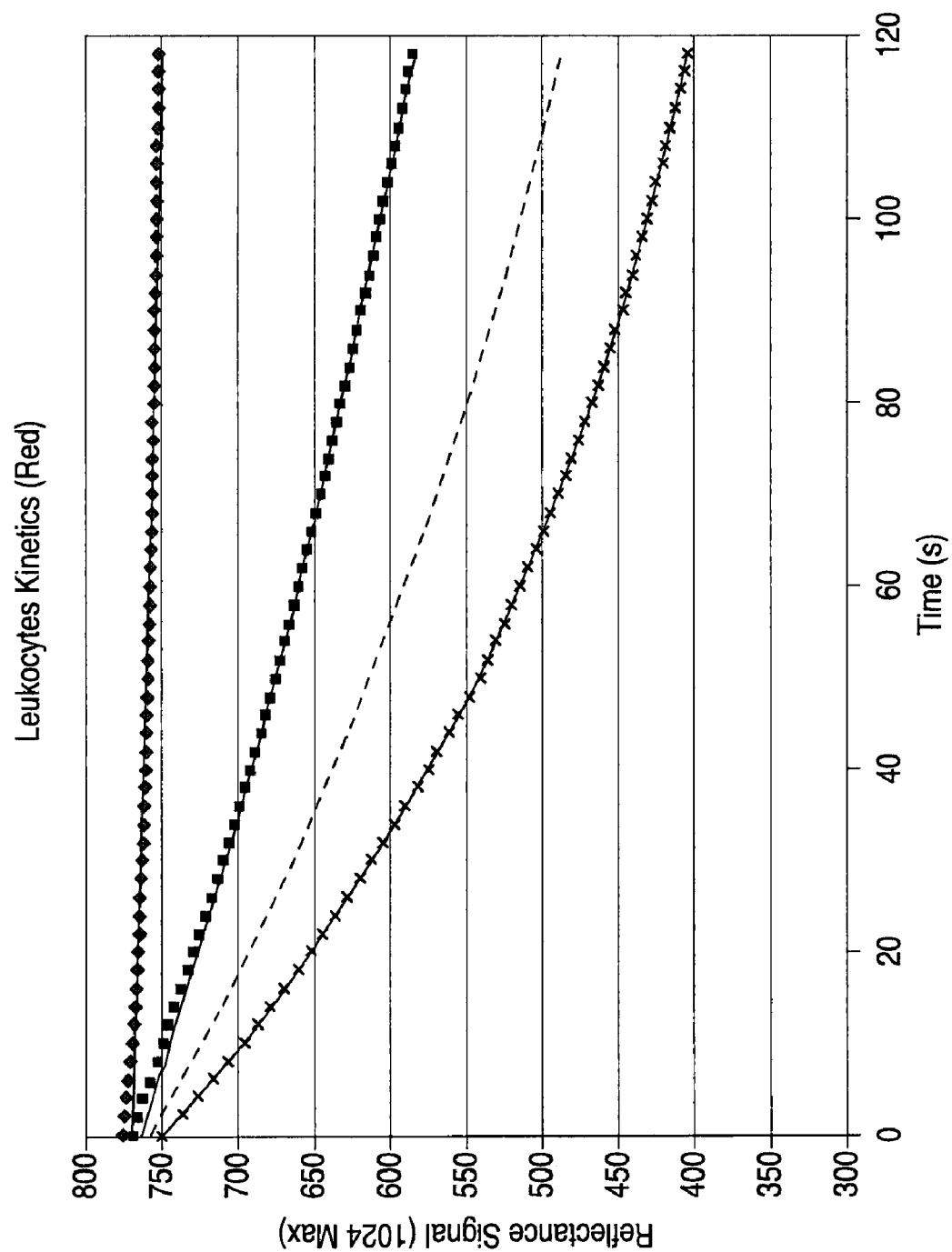
FIG. 4 is a graph showing a plot of reflectance over time during the incubation period.

For example, FIG. 4 is a graph showing a plot of reflectance vs time measured from a leukocyte pad on a chemistry strip when illuminated sequentially by red LEDs (~630 inn) over a period of two minutes. The reflectance R(t) is observed to decrease over time, fitting well to a kinetic model defined by $R(t)=A\exp[-B(t+t_o)]+C$. This same plot also compares reflectance acquired from pads initially dosed with different concentrations of leukocytes. By inspection, the slope of R(t) at time=$-t_o$, which is equal to B*A in the model, is greater for higher leukocyte concentrations, and the asymptotic value of R(t), equal to C in the model, is less. Thus, processor 16 makes use of both of these correlations by measuring the reflectance from the pad continually over time and fitting to the kinetic model to make a determination of concentration.

Processor 16 can utilize both the "pseudo-chromaticity" coordinates, as well as the kinetic model fit parameters, to determine concentration values for the test solution. For example, the calculated pseudo-chromaticity coordinates and the kinetic model fit parameters can be feature inputs to a suitable neural network, which then calculates the analyte concentration based on the value of all the feature inputs collectively. The configuration, operation and training of neural networks for specimen analysis, classification, characterization and/or identification is known, such at that disclosed in U.S. Pat. No. 6,947,586, which is incorporated herein by reference.

It is to be understood that the present invention is not limited to the embodiment(s) described above and illustrated herein, but encompasses any and all variations falling within the scope of the appended claims. For example, the calibration targets 8 could be individual strips of material of known reflectance mounted directly to the conveyor in-between the slots that receive the chemistry strips as opposed to a plate above the conveyor. References to the present invention herein are not intended to limit the scope of any claim or claim term, but instead merely make reference to one or more features that may be covered by one or more of the claims. Materials, processes and numerical examples described above are exemplary only, and should not be deemed to limit the claims.

What is claimed is:

1. A chemistry strip reader for analyzing chemistry strips, comprising:
   a conveyor having a surface for supporting a plurality of chemistry strips in a plurality of imaging positions and for moving the chemistry strips through the imaging positions at discrete points in time;
   a camera for capturing images of a field of view that includes the plurality of imaging positions and any of the chemistry strips therein, wherein the images are captured at the discrete points in time; and
   a processor for determining reflectance values for each of the chemistry strips from the captured images at the discrete points in time;
   wherein for each of the chemistry strips, the processor is further configured to calculate a concentration determination associated therewith by:
      fitting the determined reflectance values for the chemistry strip to a curve defined by $A\exp[-B(t+t_o)]+C$, where A, B, C, and $t_o$ are fit parameters;
      determining a first slope of the curve for $t=-t_o$; and
      comparing the first slope with known first slopes for known analyte concentrations.

2. The chemistry strip reader of claim 1, further comprising:
a plurality of calibration targets of known reflectance disposed in the field of view and adjacent the imaging positions.

3. The chemistry strip reader of claim 2, wherein the processor is configured to determine reflectance of the calibration targets and to adjust the determined reflectance values for the chemistry strips in response to the detected reflectance of the calibration targets.

4. The chemistry strip reader of claim 1, further comprising:
a plate disposed between the camera and the conveyor, wherein the plate includes apertures formed therein through which the camera captures the images of the plurality of imaging positions.

5. The chemistry strip reader of claim 4, wherein the plate includes portions thereof between the apertures that form calibration targets of known reflectance.

6. The chemistry strip reader of claim 5, wherein the processor is configured to determine reflectance of the calibration targets and to adjust the determined reflectance values for the chemistry strips in response to the detected reflectance of the calibration targets.

7. The chemistry strip reader of claim 1, further comprising:
a light source configured to illuminate the field of view.

8. The chemistry strip reader of claim 7, wherein the light source includes a plurality of LEDs to produce light of different colors of illumination.

9. A chemistry strip reader for analyzing chemistry strips, comprising:
a conveyor having a surface for supporting a plurality of chemistry strips in a plurality of imaging positions and for moving the chemistry strips through the imaging positions at discrete points in time;
a camera for capturing images of a field of view that includes the plurality of imaging positions and any of the chemistry strips therein, wherein the images are captured at the discrete points in time; and
a processor for determining reflectance values for each of the chemistry strips from the captured images at the discrete points in time;
wherein for each of the chemistry strips, the processor is further configured to calculate a concentration determination associated therewith by:
fitting the determined reflectance values for the chemistry strip to a curve defined by $A \exp[-B(t+t_o)]+C$, where $A$, $B$, $C$, and $t_o$ are fit parameters;
determining a first slope of the curve for $t=-t_o$;
comparing the first slope with known first slopes for given analyte concentrations;
determining an asymptotic value of the curve; and
comparing the asymptotic value with known asymptotic values for known analyte concentrations.

10. A method of analyzing a chemistry strip comprising:
capturing a plurality of images of a chemistry strip at discrete points in time using a camera;
determining reflectance values for the chemistry strip from the captured images using a processor;
fitting the determined reflectance values for the chemistry strip to a curve defined by $A \exp[-B(t+t_o)]+C$, where $A$, $B$, $C$, and $t_o$ are fit parameters, using the processor; and
calculating a concentration determination associated with the chemistry strip using the processor by:
determining a first slope of the curve for $t=-t_o$, and
comparing the first slope with known first slopes for given analyte concentrations.

11. The method of claim 10, wherein the calculating of the concentration determination further includes:
determining an asymptotic value of the curve; and
comparing the asymptotic value with known asymptotic values for known analyte concentrations.

12. A method of analyzing a chemistry strip comprising:
placing a chemistry strip on a support surface of a conveyor;
moving the conveyor surface to sequentially move the chemistry strip to a plurality of imaging positions at discrete times;
capturing an image of the chemistry strip at each of the imaging positions using a camera;
determining reflectance values for the chemistry strip from the captured images using a processor;
fitting the determined reflectance values for the chemistry strip to a curve defined by $A \exp[-B(t+t_o)]+C$, where $A$, $B$, $C$, and $t_o$ are fit parameters, using the processor; and
calculating a concentration determination associated with the chemistry strip using the processor by:
determining a first slope of the curve for $t=-t_o$, and
comparing the first slope with known first slopes for given analyte concentrations.

13. The method of claim 12, wherein the calculating of the concentration determination further includes:
determining an asymptotic value of the curve; and
comparing the asymptotic value with known asymptotic values for known analyte concentrations.

* * * * *